(12) United States Patent
Sumian et al.

(10) Patent No.: US 6,685,927 B2
(45) Date of Patent: Feb. 3, 2004

(54) TOPICAL APPLICATION OF CHROMOPHORES FOR HAIR REMOVAL

(75) Inventors: Chryslain Sumian, Jena (DE); Wolfgang Neuberger, Labuan (MY); Serge Mordon, Villeneuve d'Ascq (FR)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/965,354

(22) Filed: Sep. 27, 2001

(65) Prior Publication Data

US 2003/0059386 A1 Mar. 27, 2003

(51) Int. Cl.⁷ .......................... A61K 7/15; A61K 7/155
(52) U.S. Cl. ............................. 424/73; 606/9
(58) Field of Search ........................................ 424/73

(56) References Cited

U.S. PATENT DOCUMENTS

| | | | |
|---|---|---|---|
| 4,654,300 A | * 3/1987 | Zuk et al. ........................ 435/7 |
| 5,292,512 A | 3/1994 | Schaefer et al. |
| 5,425,728 A | 6/1995 | Tankovich |
| 5,529,914 A | * 6/1996 | Hubbell et al. ............. 435/182 |
| 5,725,847 A | * 3/1998 | De La Mettrie et al. .. 424/70.1 |
| 6,074,385 A | 6/2000 | Klopotek |
| 6,287,549 B1 | 9/2001 | Sumian et al. |

OTHER PUBLICATIONS

Rolland A et al, "Site–Specific Drug Delivery to Pilosebaceous Structures Using Polymeric Microspheres", Pharmaceutical Research 10, 1738–1744 (1993).

Sumian C et al, "A new method to improve penetration depth of dyes into the follicular duct: Potential application for laser hair removal", Journal of American Academy of Dermatology 41, 172–175 (Aug. 99).

* cited by examiner

Primary Examiner—James M. Spear
(74) Attorney, Agent, or Firm—BJ Associates; Bolesh J. Skutnik; Thomas J. Ryan

(57) ABSTRACT

A device and method is disclosed for permanent or semi-permanent removal of hair through the activation of microparticles introduced into hair follicles. Microparticles are incorporated into a composition that is topically applied to the skin. These microparticles containing or consisting of chromophores or chemically activated molecules are of a variety of shapes and sizes. Microparticles are within a size range of 1 micron to 70 microns, and preferably between 10 and 50 microns. Microparticles of this size and variety of shapes enter hair follicles on all areas of the skin without entering other areas of the skin, such as the stratum corneum or sweat gland channels. Treatment of the skin with electromagnetic radiation, ultrasonic radiation or chemical means activates the chromophore or chemically activated compounds, thus destroying the hair follicle without damaging other areas of the skin. In another embodiment, microparticles further contain nanoparticles released further into the hair follicle by use of a solvent or other method, allowing chromophores or chemically activated molecules to penetrate deeper into the follicle and avoid structures such as the sebaceous gland.

19 Claims, 1 Drawing Sheet

TOPICAL APPLICATION OF CHROMOPHORES FOR HAIR REMOVAL

BACKGROUND OF THE INVENTION

1. Field of the Invention

The present invention relates generally to the fields of dermatology and cosmetology, and particularly relates to the application of chromophore compositions to the skin so as to target hair follicles prior to the application of electromagnetic irradiation.

2. Information Disclosure Statement

A main function of mammalian hair is to provide environmental protection. However, that function has largely been lost in humans, on whom hair is usually kept or removed from various parts of the body for cosmetic reasons.

Various procedures have been employed to remove unwanted hair, including shaving, electrolysis, the use of depilatory creams or lotions, waxing, plucking, therapeutic anti-androgens, lasers and lamps. These conventional procedures each have significant drawbacks, and most often only result in temporary hair removal. Although electrolysis or electrothermolysis can provide permanent hair removal, these painful and tedious techniques rely on operator skill and require multiple treatments. Therefore, the permanent removal of unwanted hair without the risk of the occurrence of folliculitis, scarring or infections (which often occurs after electrolysis) is difficult to achieve.

It has been disclosed that selective photothermolysis (through the use of Ruby lasers, Alexandrite lasers, Nd:YAG lasers, pulsed diode lasers, or pulsed light) is an effective method for destroying pigmented hair follicles. The thermal effects generated during laser irradiation are principally responsible for hair follicle alteration and destruction. In these procedures, thermal damage to the hair follicle is the consequence of laser light absorption by endogenous melanin. However, results are essentially dependent on hair pigmentation, quantity of melanin present in hair (depending on color, hair diameter, hair cycle, position on the body . . . etc) and the ratio between melanin concentration in the hair bulb and in the epidermis. For these reasons, hair removal methods using lasers or light alone give poor results for light-colored hairs (blond, auburn and white) and can burn and/or produce discoloration of darker skin.

Many systems have been developed to counteract these negative effects, such as cooling apparatuses, or the use of pulsed, sequenced or alternating laser pulses. In addition to pure laser applications, other methods have been disclosed, including the use of exogenous chromophore to increase the light absorption efficiency of the hair follicle in comparison with endogenous melanin absorption, and thus increase the safety of the procedure by reducing the laser power needed.

Tankovich, in U.S. Pat. No. 5,425,728, suggested that the photothermolitic effects of the lasers could be enhanced by utilizing contaminants with a high absorption of certain laser wavelength. The contaminants suggested included carbon in peach oil that, with massage or ultrasound, could be used to force the carbon into the hair ducts. For this contaminant, a $CO_2$ laser was recommended with pulses between 200 and 275 nanoseconds. An alternative method uses a near infrared laser at about 1,060 nm but with pulses in the range of 25–30 picoseconds. Another alternative utilizes a staining technique and matched the laser to the stain selected. Yet another method used a photosensitizer which made the entire hair shaft susceptible to the applied laser. These most recent laser methods using red and infrared wavelength are much quicker than the earlier treatments in that the laser can act upon a group of hairs in a fraction of a second. Also, the use of the laser is somewhat less painful and has a much lower risk of infection and scarring than any of the non-laser methods mentioned above. However, these previous carbon-based formulations are not able to specifically target hair follicles. (for example, carbon particles are found within stratum corneum).

In the patent to Schaefer, U.S. Pat. No. 5,292,512, it was suggested that only a particular diameter of microspheres could be used to specifically target hair follicles. In the case of human skin, Schaefer claims that microspheres with a diameter greater than 10 $\mu$m do not settle into the follicular duct, whereas microspheres with a size smaller than 3 $\mu$m penetrate both the stratum corneum and the follicular duct. As a result, Schaefer claims that active substances encapsulated in microspheres within this size range can be specifically targeted to the hair follicle. Rolland A et al., "Site-specific drug delivery to pilosebaceous structures using polymeric microspheres", Pharmaceutical Research 10: 1738–44 (1993) clearly demonstrated this by following the localization process of fluorescent microspheres to hair follicles. Small microspheres (<1 $\mu$m in diameter) entered into follicles as well as the upper 2–3 cellular layers of the stratum corneum and thus appeared to be spread over the skin. In contrast, medium size microspheres (around 5 $\mu$m) entered in the follicles but did not penetrate the upper layers of the stratum corneum. This results in an apparent targeting of these microspheres to hair follicles. Large microspheres (>10 $\mu$m) were excluded from penetrating into either of these sites. Consequently, appropriate choice of particle size facilitates specific follicular targeting. However, these particles can only penetrate the follicle to depths corresponding to 200–300 $\mu$m below the skin surface, which is not sufficient to destroy cells in the root of the follicle. Also, these particles still can still enter and cause damage to other areas of the skin, such as the channels of sweat glands.

Photosensitizers and, in general, exogenous compounds used in conjunction with light (exogenous chromophores) are not considered an "active substance" (these compounds are only "active" under light) and one other approach was described to encapsulate at least one exogenous chromophore in this microsphere size range (3–10 microns in diameter) to obtain specific follicular targeting before laser irradiation. This approach is described in U.S. Pat. No. 6,287,549 by Sumian et al. However, Sumian C et al. reports in "A new method to improve penetration depth of dyes into the follicular duct: Potential application for laser hair removal", J. Am. Acac. Dermatol., 41:172–5 (1999), that dyes (e.g. Rhodamine 6G) can be specifically positioned in the follicle if the dye is encapsulated in size-defined microspheres (around 5 $\mu$m in diameter) and diffusion outside the microspheres is induced. This diffusion can reach 500 $\mu$m below the skin surface (with the appropriate vehicle). After diffusion, compounds may stay in hair follicles to induce a specific action and/or diffuse into the dermal tissue. Penetration and diffusion of compounds/drugs inside hair follicles depends on the formulation vehicle and the molecule's ability to pass through a collapsed follicle, particularly its size, molecular weight and solubility. Even if diffusion occurs, the compound/drug flux is limited by those follicles that have collapsed after the initial hair removal. In addition, these microparticles do not only target the hair follicle; some microparticles can be found in the channels of sweat glands. Because sweat glands help to regulate body temperature by manufacturing and excreting sweat onto the skin surface, alteration of their excretory channels after laser irradiation can produce a "dangerous" temperature deregulation of the body, and is thus an occurrence that should be avoided.

Klopotek, U.S. Pat. No. 6,074,385, discloses a method in which magnetic particles are utilized to remove hair. Hair is first manually removed from the follicles, then particles are applied to the skin by a method that will force the particles into the follicle, such as including them in a dry slurry or a lotion. Another method would be to force them into the skin using a magnetic field. A composition consisting of magnetic particles of a size small enough (5 Angstroms-100 microns, preferably 50 Angstroms-10 microns) so that at least some of them will fit in the follicle. A magnetic field is then applied to the treatment area, which causes the particles to heat up and destroy the papilla or other vital structure in the hair follicle.

The prior art teaches the use of microparticles in hair removal, but does not disclose an effective method for preventing absorption of microparticles in other areas of the skin, such as sweat gland channels. The act of rubbing the particles, whether in a dry or other type of composition, may cause some particles to be imbedded in the skin in areas other than the follicle. This could result in damage to or discoloration of the skin. Because chromophores are not efficiently targeted to the hair follicle, only a small portion of the applied energy is actually absorbed by the follicle, and the rest is absorbed by the skin. Thus, unless the energy applied is localized to an individual hair follicle (which is very time-consuming), present applications allow absorbing particles to enter other parts of the skin and cause damage. In order to induce only hair follicle injury without damaging surrounding tissues, greater hair follicle specificity is needed. By increasing both the quantity of chromophore delivered into the follicle and the penetration depth of the chromophore into the follicular duct, the efficacy of hair removal could be improved independent of hair color.

For the foregoing reasons, there is a need to develop new methods that are efficiently and easily administered, non-irritating, able to primarily target hair follicles, and capable of depositing chromophore deeply along the hair follicles to reduce or prevent hair regrowth.

OBJECTIVES AND BRIEF SUMMARY OF THE INVENTION

It is an object of the present invention to provide a method for microparticle follicle targeting that addresses the deficiencies in the prior art.

It is another object of the present invention to provide topical compositions able to primarily target hair follicles after the removal of hair from the follicles, and thus provide compositions able to selectively introduce compounds or drugs into hair follicles.

It is a further object of this invention to provide a method where microparticles can be introduced into hair follicles without being absorbed by other appendages of the skin.

It is yet another object of this invention to provide a method where particles can be introduced that solely target the hair follicle, while leaving the sebaceous gland unaffected.

It is another object of the present invention to provide topical compositions able to selectively introduce photosensitizers and/or sonosensitizers into hair follicles prior to the application of electromagnetic irradiation on the area to be treated, and thus reduce or prevent the regrowth of hair.

It is still another object of the present invention to provide topical compositions containing different size and/or shape of microparticles to target all diameters and shapes of hair follicles.

Briefly stated, the present invention provides a device and method for permanent or semi-permanent removal of hair through the activation of microparticles introduced into hair follicles. Microparticles are incorporated into a composition that is topically applied to the skin. These microparticles containing or consisting of chromophores or chemically activated molecules are of a variety of shapes and sizes. Microparticles are within a size range of 1 micron to 70 microns, and preferably between 10 and 50 microns. Microparticles of this size and variety of shapes enter hair follicles on all areas of the skin without entering other areas of the skin, such as the stratum corneum or sweat gland channels. Treatment of the skin with electromagnetic radiation delivered by a laser or a non-coherent radiation-emitting lamp, ultrasonic radiation or chemical means activates the chromophores or chemically activated molecules, thus destroying the hair follicle without damaging other areas of the skin. In another embodiment, microparticles further contain nanoparticles released further into the hair follicle by use of a solvent or other method, allowing chromophores or chemically activated molecules to penetrate deeper into the follicle and avoid structures such as the sebaceous gland.

The above, and other objects, features and advantages of the present invention will become apparent from the following description read in conjunction with the accompanying drawings.

DETAILED DESCRIPTION OF THE PREFERRED EMBODIMENT

Figure 1:
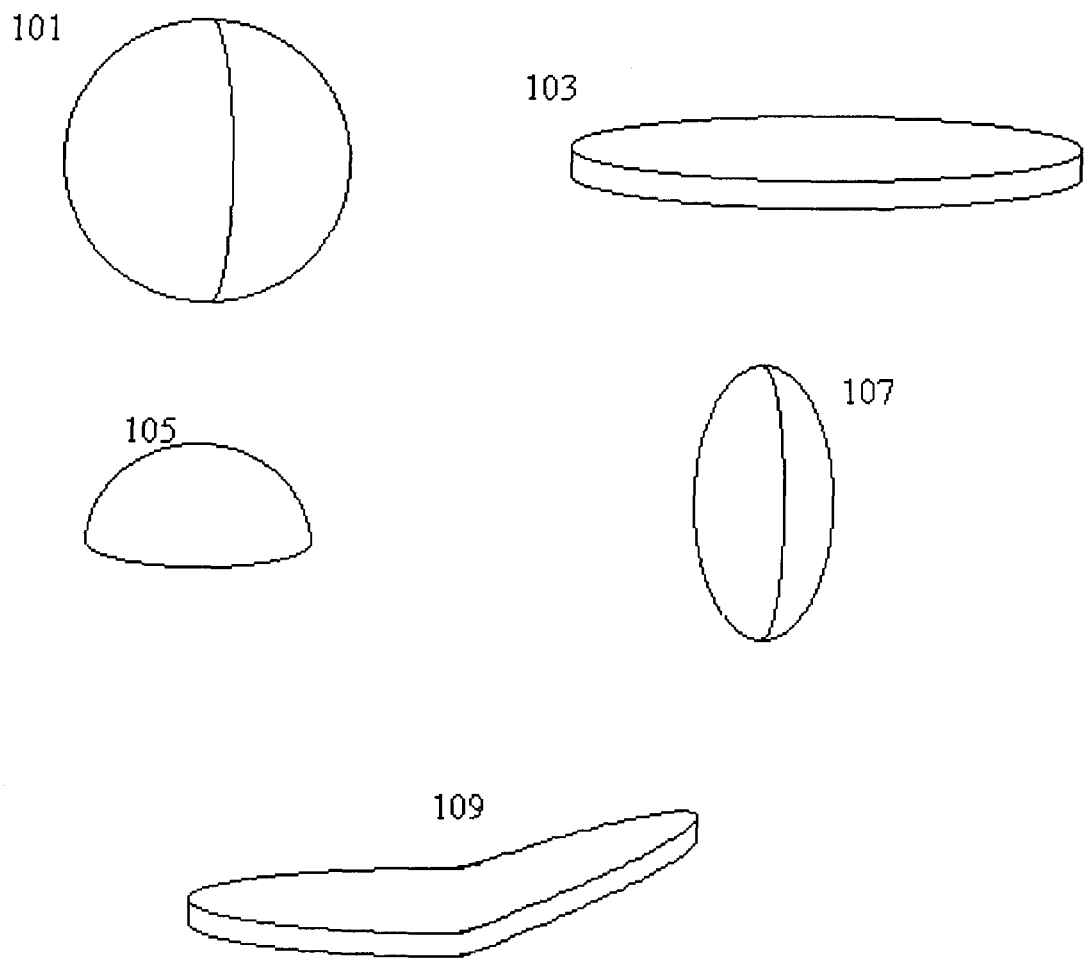
FIG. 1—An illustration describing possible microparticle shapes.

The present invention involves the topical application of a composition containing chromophores, incorporated in or forming microparticles of different sizes and shapes, to reduce or avoid hair regrowth after one or more treatments with electromagnetic radiation, ultrasonic radiation, or chemical application. Utilizing microparticles with a variety of sizes and shapes allows penetration into hair follicles on different areas of the skin without penetrating other areas of the skin. Specifically, microparticles with sizes in the range of 10–50 microns allow penetration into the hair follicles while excluding microparticles from the stratum corneum or the sweat gland channels.

The microparticles used in the present invention achieve permanent hair removal through the presence of pharmaceutically or chemically activated compounds and chromophores. Chromophores are compounds or substances that are active under electromagnetic or ultrasonic irradiation and without direct activity alone. The types of chromophores typically used include photosensitizers, sonosensitizers, and compounds active under other electromagnetic radiation. Photosensitizers are substances that generate chemical or thermal effects under monochromatic or polychromatic light irradiation and sonosensitizers are substances that generate chemical or thermal effect under ultrasonic irradiation.

The types of chromophore compounds that can be used in the present invention include any molecules used in cosmetic and/or pharmaceutics fields, including all photosensitizer molecules, their derivatives, and their precursors used in photodynamic therapy and including all sonosensitizer molecules, their derivatives, and their precursors used in sonodynamic therapy.

Chromophores used in conjunction with this invention are introduced into the hair follicle via the use of microparticles contained in a composition for topical application to the skin. These microparticles may be manufactured by any known process. Examples of such manufacturing processes include monomer polymerization or dispersion of preformed natural or synthetic polymers. Liposomes or polymerized liposomes can also be used with the present invention.

Chromophores or other activating compounds can be incorporated into the microparticles in a variety of ways. The compounds can be encapsulated into microparticles or can form the microparticles themselves. Also, microparticles can be impregnated with and/or coated with compounds. In all cases, microparticles produced or utilized for this invention are limited to a specific size range.

The sizes of microparticles can range from 1 to 70 microns and preferably range from 10–50 microns. The microparticles contained in the formulation have different sizes and can also have different shapes. There is no limitation on the geometric shapes of the microparticles, and the size may vary without limitation provided they are within the above described size range. Microparticles used in the present invention can also be vesicular. Examples of shapes that could be used include spheres, cylinders, ovoid or egg-shaped microparticles, cubes, and pyramids. The sizes of these microparticles are defined by the maximum dimension that these microparticles have. For example, if these microparticles are disc shaped, the maximum size will be the diameter of the disc (in comparison with the thickness of this disc). In one preferred embodiment, microparticles have different size, in the limit of the present invention, to target all hair follicles present on the body without limitation on their diameters.

Examples of the potential shapes of the microparticles are illustrated in FIG. 1. Shape 101 is a typical spherical microparticle, or microsphere. Previous inventions have utilized this shape, but it has been necessary to use microparticles of a much bigger diameter than the diameter of sweat gland channels to target only the hair follicle. A number of non-spherical shapes can effectively and specifically target hair follicles. These shapes are modeled after the types of deformation of the shaft opening after the hair is removed. For example, shapes such as a disc (103), a hemisphere (105), or a pill shape (107) can all be utilized in addition to the sphere shape to approximate the potential shape of the hair follicle and to increase the quantity of microparticles placed into the hair follicle. In the alternative, the microparticles may be flexible (109), accommodating further possible follicle shapes, and resulting in even more efficient microparticle penetration.

Microparticles are then incorporated into any cosmetically and/or pharmaceutically acceptable composition by which the microparticles can be introduced into the hair follicle. Such compositions include salts, drugs, medicaments (substances used in therapy), inert ingredients or other materials. Any such embodiment may be used, so long as it is suitable for use in contact with the tissues of humans or other animals without an unreasonable risk of inducing toxicity, incompatibility, instability, irritation, allergic response, and the like reactions. At least 90% of the total weight of the microparticles used in a composition must be due to microparticles within the invention's preferred 10–50 micron size range.

The present invention is accompanied by a method for permanent or semipermanent depilation on body areas of an animal or human. A composition containing a specific size range of microparticles is topically applied, comprising the following steps:

1. Unwanted hair is removed by any known method from the targeted area of skin from which hair removal is desired.
2. A cosmetically and/or pharmaceutically acceptable composition, consisting of microparticles of a size between 1 to 70 microns, preferably between 10 to 50 microns, and containing active compounds/drugs, is topically applied to the targeted area of skin.
3. Excess composition is then removed from the skin, leaving only those microparticles that have penetrated the hair follicles.
4. In an optional additional step, ultrasonic waves are applied to the treatment area. These waves cause the chromophore or microparticle to be driven further into the hair follicle. This step could also be performed after Step 5, so as to drive the compounds or drugs further into the follicle after they are released from the microparticle.
5. Releasing compounds or drugs contained within the microparticles into the hair follicles.
6. Activating the compounds by electromagnetic irradiation, ultrasonic irradiation, chemical or thermal processes, or other known methods, thus altering and/or killing cells responsible for hair growth.

The above steps are further explained as follows. Hair is removed from the follicles in Step 1 using any known method, such as cold waxing, warm waxing, or the use of mechanical devices.

In Step 2, topical application may be accomplished by directly laying or spreading the composition on the skin of a human or other mammal. This application could be performed with massaging. After this application, a substance, film, dressing or other means could be applied to achieve an occlusion (to close the area).

Examples of photosensitizer molecules that could be used in the microparticles include methylene blue, hematoporphyrin, indocyanine green, microcyanine, clorin, chlorophyll, dyes, carbon, ALA (aminolevulinic acid), benzoporphyrin, protoporphyrin and their derivatives. In one preferred example, amphiphilic photosensitizers are used in the microparticles. Examples of sonosensitizer molecules that could be used in the microparticles include all photosensitizer molecules, mesoporphyrin, gallium porphyrin analogue, aluminium phtalocyanines and their derivatives. The list of photosensitizer and sonosensitizer molecules given here is for illustrative purposes and is not limited to these examples.

In Step 3, removal of excess composition from the skin is typically performed by cleaning the skin with gauze. Additional composition can be added to more effectively clean the skin surface.

In Step 5, "release" refers to the diffusion of compounds from the microparticles into the hair follicle and surrounding tissue. This diffusion is obtained by any known means and will vary depending on the type of chromophore or other compound used in the microparticles. Examples of such means include microparticle biodegradation, microparticle dissolution in situ possibly induced by topical application of a solvent, optical reactions, temperature change, physical processes or physiological reactions. The list of processes given here is non-limiting and is given only for illustration.

In Step 6, electromagnetic irradiation can include electromagnetic or ultrasonic irradiation. Electromagnetic radiation can successfully activate the chromophore by monochromatic irradiation produced by lasers or polychromatic irradiation produced by lamps. The use of non-laser irradiation can be advantageous in that polychromatic radiation could produce a more effective activation of the photosensitizer compound in those instances where the application of a solvent or other surrounding parameters alters the compound's absorption maximum. Also, non-laser sources can be cheaper and safer for use. Chemical effects include photodynamic therapy or sonodynamic therapy in which photosensitizers or sonosensitizers are used.

There are numerous advantages to using this method over the use of a formulation containing only one specific microparticle size and shape. The first advantage stems from the fact that the size of the hair follicle varies with location on the body. It is also known that the shape of a hair follicle may deform, particularly because of follicle collapse after mechanical removal of hair. As a result, microparticles of fixed size and shape are limited to certain areas of the body containing hair follicles of a specific size, and are further limited by those follicles which have deformed so as to exclude those microparticles. Using the present invention, it is possible to target all hair follicle diameters in all areas of the body with the same formulation. This will also simplify the manufacturing process, in that it would be no longer necessary to perform high filtration to isolate a particular size microparticle.

Another advantage over previous inventions, particularly because those inventions generally require a microparticle size between 3 and 10 microns, is that the microparticle of a larger size cannot penetrate the skin and are more easily removed from the skin. Also, the size of the microparticle prevents them from entering into the sweat gland channel, thus avoiding possible damage upon irradiation.

Another embodiment of the present invention involves the use of a composition containing microparticles with different sizes and shapes, in the range defined by the present invention, containing chromophore that is encapsulated in nanoparticles. Nanoparticles are particles that are of a size in the range of 1 to 1,000 nanometers. In this embodiment, the microparticles penetrate the hair follicle as in the previous embodiment. The accompanying method comprises the following steps:

1. Unwanted hair is removed by any known method from the targeted area of skin from which hair removal is desired.
2. A cosmetically and/or pharmaceutically acceptable composition, consisting of microparticles of a size between 10 to 50 microns comprising nanoparticles that contain compounds or drugs, is topically applied to the targeted area of skin.
3. Excess composition is then removed from the skin, leaving only those microparticles that have penetrated the hair follicles.
4. Releasing the nanoparticles from the microparticles by any known method, then allowing time for the nanoparticles to settle and penetrate deeper into the hair follicle.
5. Releasing compounds or drugs contained within the nanoparticles into the hair follicles.
6. Activating the compounds by electromagnetic irradiation, ultrasonic irradiation, chemical or thermal processes, or other known methods, thus altering and/or killing cells responsible for hair growth.

In Step 4, the nanoparticles can be released, for example, by the use of a solvent. Steps 1–3 and Steps 5 and 6 are identical to those described in the previous embodiment. The discussion of those steps in the previous embodiment also apply to this embodiment.

There are additional advantages to using this alternative embodiment. First, after the release of chromophore-loaded nanoparticles into the hair follicle, those nanoparticles are not able to penetrate the cell membranes due to their size. Thus, these nanoparticles are only localized in hair follicle and cannot contaminate the surrounding tissue, such as the epidermis, dermis, or hypodermis. Second, toxicity without electromagnetic irradiation is reduced. Lastly, the chromophore could be released from the nanoparticles more deeply in the hair follicle, thus targeting only deep cells within the follicle. For example, this embodiment can be employed to avoid release of the chromophore in the sebaceous gland.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A composition for permanent/semi-permanent hair removal comprising non-spherical microparticles wherein a majority of said microparticles are of a size not less than 10 microns and not greater than 50 microns, wherein said size of said microparticle is measured along said microparticle's largest dimension, and wherein further said microparticles are activatable to destroy hair follicles.

2. A composition according to claim 1, wherein said microparticles are capable of entering hair follicles of all sizes and shapes without penetrating other areas of the skin.

3. A method for permanent/semi-permanent hair removal using a composition comprising microparticles, comprising the steps of:
   a. removing hair from the follicles in an area of skin to be treated by a known method;
   b. topically applying said composition to said area of skin so that said microparticles enter follicles of various shapes and sizes but do not enter other parts of the skin;
   c. removing excess composition from said area of skin, leaving only said composition that has entered said follicles; and
   d. activating compounds and destroying said follicles with a treatment of electromagnetic irradiation by means of a non-laser radiation source, wherein said non-laser radiation source is selected from the group consisting a light-emitting diode, a superluminescent diode, and a lamp emitting polychromatic radiation.

4. The composition according to claim 1, wherein said microparticles comprise compounds selected from the group consisting of chromophores, photosensitizers, sonosensitizers, and compounds activated by chemical reaction.

5. The composition according to claim 4, wherein said compound is preferably methylene blue.

6. The composition according to claim 1, wherein said microparticles are flexible.

7. The composition according to claim 1, wherein said microparticles are vesicular.

8. A composition for permanent/semi-permanent hair removal comprising microparticles wherein:
   a majority of said microparticles are of a size greater than 10 microns;
   said microparticles comprise compounds selected from the group consisting of chromophores, photosensitizers, sonosensitizers, and compounds activated by chemical reaction; and said microparticles contain nanoparticles, wherein said nanoparticles consist of said compound.

9. The composition according to claim 1, wherein at least 90% of the total weight of said microparticles comprises microparticles of a size not less than 10 microns and not greater than 50 microns, wherein further said size of said microparticle is measured along said microparticle's largest dimension.

10. A method for permanent/semi-permanent hair removal using a composition comprising microparticles of a size greater than 10 microns, comprising the steps of:
   a. removing hair from the follicles in an area of skin to be treated by a known method;
   b. topically applying said composition to said area of skin so that said microparticles enter follicles of various shapes and sizes but do not enter other parts of the skin;
   c. removing excess composition from said area of skin, leaving only said composition that has entered said follicles; and
   d. activating compounds and destroying said follicles with a treatment selected from the group consisting of electromagnetic irradiation, ultrasonic irradiation, and solvent/chemical application.

11. The method according to claim 10, wherein step c. comprises the steps of:
   c1. removing excess composition from said area of skin, leaving only said composition that has entered said follicles; and
   c2. releasing compounds from the microparticles by means other than electromagnetic irradiation.

12. The method according to claim 10, wherein said microparticles are non-spherical.

13. The method according to claim 10, wherein at least 90% of the total weight of said microparticles comprises microparticles of a size not less than 10 microns and not greater than 50 microns, wherein further said size of said microparticle is measured along said microparticle's largest dimension.

14. The method according to claim 10, wherein said electromagnetic irradiation is delivered by means chosen from the group consisting of a laser emitting monochromatic radiation and a non-laser radiation source, wherein further said non-laser radiation source is selected from the group consisting of a light-emitting diode, a superluminescent diode, and a lamp emitting polychromatic radiation.

15. A method for permanent/semi-permanent hair removal using a composition comprising microparticles, wherein said microparticles contain nanoparticles, comprising the steps of:
   a. removing hair from the follicles in an area of skin to be treated by a known method;
   b. applying said composition to said area of skin so that said microparticles enter follicles of various shapes and sizes but do not enter other parts of the skin;
   c. removing excess composition from said area of skin, leaving only said composition that has entered said follicles;
   d. releasing said nanoparticles from said microparticles further into said hair follicles; and
   e. activating said compounds from said nanoparticles and thus destroying said follicles with a treatment selected from the group consisting of electromagnetic irradiation, ultrasonic irradiation, and solvent/chemical application.

16. The method according to claim 15, wherein said microparticles are non-spherical.

17. The method according to claim 15, wherein at least 90% of the total weight of said microparticles comprises microparticles of a size not less than 10 microns and not greater than 50 microns, wherein further said size of said microparticle is measured along said microparticle's largest dimension.

18. The method according to claim 15, wherein said electromagnetic irradiation is delivered by means selected from the group consisting of a laser emitting monochromatic radiation and a non-laser radiation source, wherein further said non-laser radiation source is selected from the group comprising a light-emitting diode, a superluminescent diode, and a lamp emitting polychromatic radiation.

19. The method according to claim 10 or 15, comprising the further intermediate step of:
   applying ultrasonic radiation to said area of skin to drive said microparticles further into said follicles prior to activation steps.

* * * * *